United States Patent [19]
Schäfer et al.

[11] Patent Number: 5,861,097
[45] Date of Patent: Jan. 19, 1999

[54] METHOD AND DEVICE FOR PREPARING SAMPLES

[75] Inventors: Helwig Schäfer, Herisau, Switzerland; Wolfgang Frenzel, Berlin, Germany

[73] Assignee: Metrohm AG, Herisau, Switzerland

[21] Appl. No.: 897,086

[22] Filed: Jul. 18, 1997

[30] Foreign Application Priority Data

Jul. 26, 1996 [CH] Switzerland ............ 1869/96

[51] Int. Cl.⁶ ............................................ B01D 15/08
[52] U.S. Cl. .................... 210/635; 210/651; 210/656; 210/198.2
[58] Field of Search ................ 210/656, 635, 210/644, 649, 650, 651, 659, 198.2; 436/161

[56] References Cited

U.S. PATENT DOCUMENTS

| | | | |
|---|---|---|---|
| 4,451,374 | 5/1984 | Peterson | 210/656 |
| 4,491,011 | 1/1985 | Nordmeyer et al. | 210/656 |
| 4,529,521 | 7/1985 | Cortes et al. | 210/656 |
| 4,584,276 | 4/1986 | Hanaoka | 210/656 |
| 4,689,152 | 8/1987 | Liang | 210/656 |
| 4,715,217 | 12/1987 | Coyne | 210/656 |
| 4,726,930 | 2/1988 | Matsushita | 210/656 |
| 4,837,157 | 6/1989 | Turnell | 210/656 |
| 4,837,161 | 6/1989 | Stevens | 210/656 |
| 4,891,137 | 1/1990 | Nohl | 210/656 |
| 5,160,625 | 11/1992 | Jonsson | 210/656 |
| 5,221,477 | 6/1993 | Melcher | 210/656 |
| 5,279,972 | 1/1994 | Heckenberg | 210/656 |

FOREIGN PATENT DOCUMENTS

| | | | |
|---|---|---|---|
| 1 528 430 | 6/1967 | France | 210/656 |
| 1 573 147 | 5/1968 | France | 210/656 |

OTHER PUBLICATIONS

Martinez, "Membrane extraction" Analytica Chimica Acta, 304 (1995) pp. 323–332.

*Primary Examiner*—Ernest G. Therkorn
*Attorney, Agent, or Firm*—Shoemaker and Mattare, Ltd.

[57] ABSTRACT

From an analysis probe to be analyzed, impurities such as proteins or solid matter are separated from the analytes to be analyzed by way of dialysis. An analysis solution containing the analytes is separated from an acceptor solution by a membrane of a dialysis cell. The membrane is chosen such that the analytes diffuse from the analysis solution through the membrane into the acceptor solution. In order to maintain as high as possible concentration of analytes in the acceptor solution, the analysis solution is constantly renewed. The acceptor solution remains stationary in an acceptor chamber until the concentration of analytes in the acceptor solution has reached a predetermined value, for example 95%.

7 Claims, 3 Drawing Sheets

METHOD AND DEVICE FOR PREPARING SAMPLES

BACKGROUND OF THE INVENTION

The invention relates to a method and a device for preparing samples for a chemical analysis method, in particular for chromatography, according to the preamble of the independent patent claims.

As a preparation for carrying out chemical analysis methods such as for example chromatography or flow techniques, the sample to be analysed must be prepared. Analysis samples contain, in addition to the ions or molecules (analytes) to be determined, impurities, particularly larger molecules or solid components which may lead to adulterated analysis results. These impurities must be removed from the analysis sample before the analysis method. Impurities which commonly occur are for example proteins with the analysis of food or filter fibres, dust particles or likewise with analysis in the field of the environment.

For removing these molecules or solid material from the analysis sample, various methods are known. The analysis samples may be prepared by the addition of acid for example and by centrifuging or filtration. From U.S. Pat. No. 5,279,972 and U.S. Pat. No. 4,837,157, separating methods by way of dialysis are known. According to the method of U.S. Pat. No. 4,837,157, the analysis solution and the acceptor solution are moved on both sides of a permeable membrane. The permeable membrane is chosen such that the analytes to be determined may migrate through the membrane, and that the impurities to be excluded from the analysis are kept back by the membrane. A problem with this known method lies in the fact that the acceptor solution containing the analytes may never achieve as high a concentration of analytes as in the original analysis solution. The analytes migrate at a maximum through the membrane into the acceptor solution until an equal concentration on both sides of the membrane is to be established. The concentration of the analytes in the acceptor solution thus comprises at the most, a value of 50%. This is above all disadvantageous then, when various analytes are present in the analysis solution. Ions of different sizes do not migrate with the same speed through the membrane. These theoretical concentration values of 50% are only achieved with very long dialysis times of up to a few hours. In the average case, chloride for example is only enriched to 10% to 30% and sulphate only to 5% to 10% in the acceptor solution. With the occurrence of various analytes there results, because of this, inaccuracies with regard to the ratio of concentrations of the individual analytes. Difficult or only inaccurately reproducable anaylses are the result thereof.

From Martinez et al. (membrane extraction—preconcentration cell coupled on-line to flow injection and liquid chromatographic system. Determination of triazines in oil. Analytica Chimica Acta 304 (1995) 323–332) a membrane extraction is known, in which the acceptor solution is kept still in the acceptor cell for a certain period of time. By way of a directed choice of acceptor solution, the analytes migrated into the acceptor solution are converted (protonized) so that the concentration of unaltered analytes in the acceptor solution constantly remains at a low value. In this manner a gradient is produced which permits the continued diffusion of analytes into the acceptor solution. The disadvantage with this method lies in the fact that to carry out the actual analysis, the converted analytes must be brought back into the original form. This gives rise to an additional method step and increases the danger of losses or measuring errors. Furthermore the method known from Martinez et al cannot easily be applied to the analysis of ions. Whilst Martinez et al procedes from basic organic molecules which are simply removed from equilibrium in a column by protonation, no such simple reactions are possible for ions.

BRIEF SUMMARY OF THE INVENTION

The object of the present invention lies in preventing the disadvantages of that which is known, in particular to provide a method and a device for preparing samples for an analysis method which permits a high dialysis rate, and thus in a simple manner, allows an economical and fast preparation of samples for analysis methods. According to the invention this object is achieved by a method and a device with the features of the latter part of the independent patent claims.

With a method for preparing samples for a chemical analysis method, in particular for chromatography or for flow techniques, the analytes of an analysis solution are separated from the impurities (for example proteins or carbon fibres) contained in the analysis solution by way of dialysis. For this, the analysis solution is added to a sample chamber and a determinable quantity of the acceptor solution is added into an acceptor circuit of a dialysis cell. The acceptor circuit and the sample chamber are separated from one another by a permeable membrane which is chosen such that the analytes may migrate through the membrane from the sample chamber into the acceptor circuit. This migration, directed towards the acceptor chamber, takes place as long as the concentration of the analytes in the sample chamber is larger than in the acceptor circuit. Essential to the invention is that fresh analysis solution is continuously delivered into the sample chamber, so that the concentration of analytes in the sample chamber constantly has a value of almost 100%. The acceptor solution is added into the acceptor circuit and kept in this so that no renewal of the acceptor solution takes place. Since the concentration of the analytes in the sample chamber continuously has a value of almost 100%, there then arises an equilibrium only when the concentration in the acceptor chamber also reaches a value of almost 100%. On reaching this value, the acceptor solution may be removed from the acceptor circuit and supplied to an analysis apparatus.

Acceptor circuit is to be understood as an acceptor chamber of a dialysis cell which is closable against the supply of new acceptor solution. A device which shorts the acceptor chamber at both its ends to an acceptor circuit is conceivable. It is however also possible to design the acceptor circuit closable at both its ends. In the following, under the heading acceptor circuit, both possibilities are summarized.

Fresh analysis solution is to be understood as a solution which comprises the same concentration of analytes as the unprepared analysis or sample solution.

The concentrations given in percentage relate to the concentration of the analytes in the original analysis solution. The longer the acceptor solution is left in the acceptor chamber, the higher are the concentration values which can be achieved. In a particularly advantageous method, the analysis solution is pumped through the sample chamber until the concentration of acceptor solution has a value of almost 100% (at least 95%). Typically, analysis times of 4 to 12 minutes are to be seen as sufficient for achieving a concentration which is satifactory for the subsequent analysis method.

This preparation method is particularly favourable as a preparation for subsequent chromatography. It may however also be used for other analytical methods in which a separation of matter contained in a solution must be achieved.

For achieving the previously mentioned analysis times and concentration values, the flow of the analysis solution in a particularly favourable embodiment example is between 0.01 and 10 milliliters per minute, preferably 0.8 milliliters per minute.

Very generally, sample chamber is to be understood as a receptacle suitable for receiving the analysis solution or a region which is flown through by the sample solution. It is conceivable to carry out the method according to the invention with sample and acceptor chambers of different shapes and dimensions. Thus for example, an acceptor chamber, delimited to the outside by a dialysis membrane, may be employed as a probe and submersed into an agitated analysis sample. The sample chamber may in this case be formed e.g. by a fluid stream (such as a water course) or by thoroughly mixed samples in a container. By immersion of such a probe into a flowing medium, it is automatically guaranteed that the dialysis membrane on one side is constantly in contact with fresh analysis solution. The same happens on immersion of the probe in a constantly thoroughly mixed receptacle. Such probes may be taken out of the sample chamber, for instance from the flowing medium, after the dialysis has been effected. The acceptor solution is removed from the probe and supplied to an analysis apparatus. The probe may of course also be used as a separate sample taking device. With the use of the acceptor chamber as a probe, the acceptor chamber and the sample chamber are physically separated from one another. At the same time, the measuring device comprises essentially of the acceptor circuit closed by the membrane. With this, a tube or spherical-shaped acceptor circuit may be employed. The acceptor circuit may be formed closable or directly connectable to an analysis apparatus via a valve arrangement. Instead of maintaining the sample solution in constant motion (by the supply of new sample solution or by mixing) it is also conceivable to move the acceptor chamber through a static sample solution.

Essential to the invention is that the one side of the dialysis membrane is in constant contact with the analysis solution with an approximate hundred percent concentration, whilst the other side of the membrane remains in contact with the originally inputted and unchanged acceptor solution until a predetermined value of the concentration of the analytes in the acceptor solution is achieved. Unchanged in this context means that the acceptor solution neither is replaced nor is converted in another compound by a chemical reaction.

The device according to the invention for preparing samples for a chemical analysis method, in particular for chromatography, comprises essentially of a dialysis cell with a sample chamber for receiving an analysis solution, and an acceptor circuit for receiving a determinable quantity of acceptor solution.

The sample chamber is construed for a continuous supply of fresh sample solution and the acceptor circuit is construed for keeping constant the inputted quantity of acceptor solution.

In a particularly advantageous embodiment form of the invention there is provided a multi-way valve for controlling the sample preparation process. At the same time the acceptor chamber of the dialysis cell may be shorted to an acceptor circuit by way of the multi-way valve.

The acceptor chamber of the dialysis cell is connected on both sides in each case to a connection of the valve. Both these connections may be connected to one another in a dialysis position during the dialysis. In the dialysis position, the acceptor chamber is closed per se, and no renewal of the acceptor solution takes place.

A particularly simple embodiment example results when in each case two of the remaining connections of the multi-way valve are connected on the one hand to the feeding of the acceptor solution and on the other hand to an analysis system. In the one analysis position of the valve, the connections connected to the acceptor chamber are connectable to connections connected to the feeding of the acceptor solution and to the analysis system. The analysis position of the valve corresponds essentially to a rinsing position which permits a flushing and cleaning of the dialysis cell. In this position the acceptor cell may be flushed with the acceptor solution.

For delivering the analysis solution and also for adding the acceptor solution into the acceptor circuit or for cleaning, a pump may be employed, preferably the pump is a double-channel tubing pump. In this manner, according to the requirements, the analysis solution only, or the analysis solution and the acceptor solution may be pumped.

It is also conceivable, for delivering the analysis solution and/or the acceptor solution, to use an injection and metering system, or by way of excess pressure to exert a gas pressure (inert gas or also air) onto a receptacle containing the analysis solution or the acceptor solution.

It has been shown that with the choice of a special shape of the acceptor chamber and of the sample chamber, particularly favourable dialysis results may be achieved. Chambers which are arranged meander-shaped, spiral and helical-shaped have proven themselves to be particularly advantageous.

BRIEF DESCRIPTION OF THE DRAWINGS

The invention is hereinafter described in more detail by way of an embodiment example and the drawings. There are shown.

DETAILED DESCRIPTION OF THE INVENTION

Figure 1:
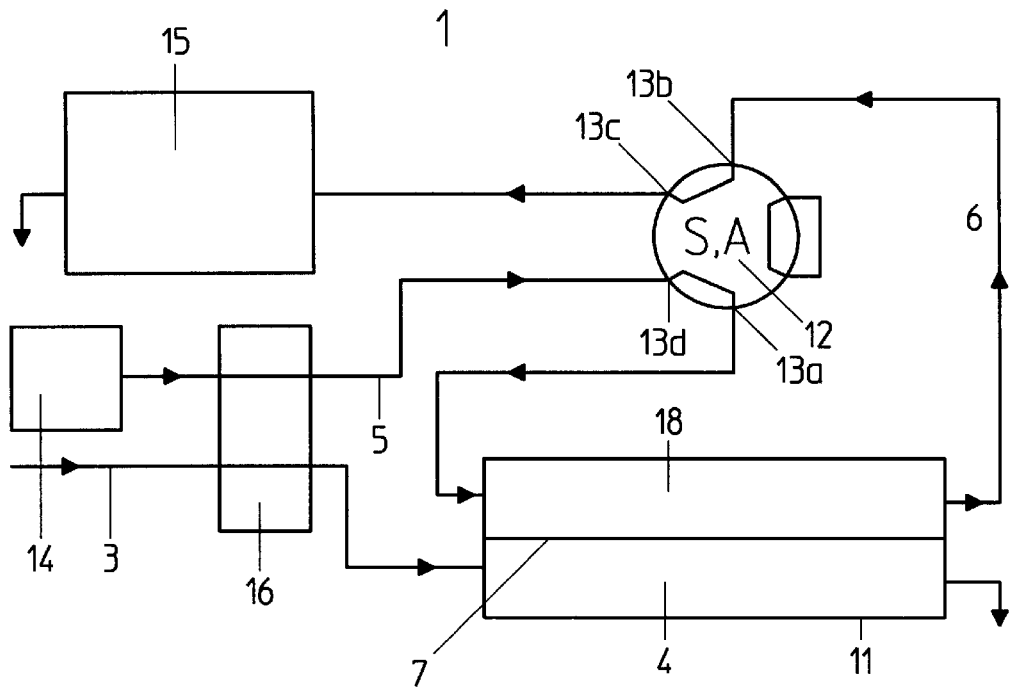
FIG. 1 a schematic representation of a device according to the invention in a rinsing or analysis position, FIG. 2 the device of FIG. 1 in a dialysis position, FIG. 3 a schematic representation of the dialysis cell of the device of FIG. 1, FIG. 4 a schematic representation of the the meander-shaped course of of the dialysis channel as an embodiment example of a dialysis cell, and FIGS. 5a and 5b a schematic representation of a further embodiment example of the device according to the invention.

FIG. 1 shows a device 1 according to the invention with a multi-way valve 12 in the rinsing position S or the analysis position A. The device 1 consists essentially of a dialysis cell 11 and the valve 12. The dialysis cell 11 comprises an acceptor circuit 6 with an acceptor chamber 18, and a sample chamber 4 which are separated from one another by a permeable membrane 7.

An analysis solution 3 containing analytes 1 of an analysis sample 2 is delivered through the sample chamber 4 of the dialysis cell 11 by way of a pump 16. Simultaneously, the acceptor chamber 18 of the dialysis cell 11 is filled with an acceptor solution 5. The pump 16 is a double-channel tubing pump and may also be employed for adding the acceptor solution 5 into the acceptor chamber 18. The acceptor chamber 18 is connected to two connections 13a, 13b of the valve 12. Two further connections 13c, 13d of the valve 12 are on the one hand connected to an analysis device 15 and on the other hand to a feeding 14 of the acceptor solution 14. In the rinsing position S or in the analysis position A, the connections 13a, 13b are each connected to one of the connections 13d, 13c.

As soon as the acceptor chamber 18 is filled with fresh acceptor solution, the valve 12 may be set from the rinsing position S into a dialysis position D.

Figure 2:
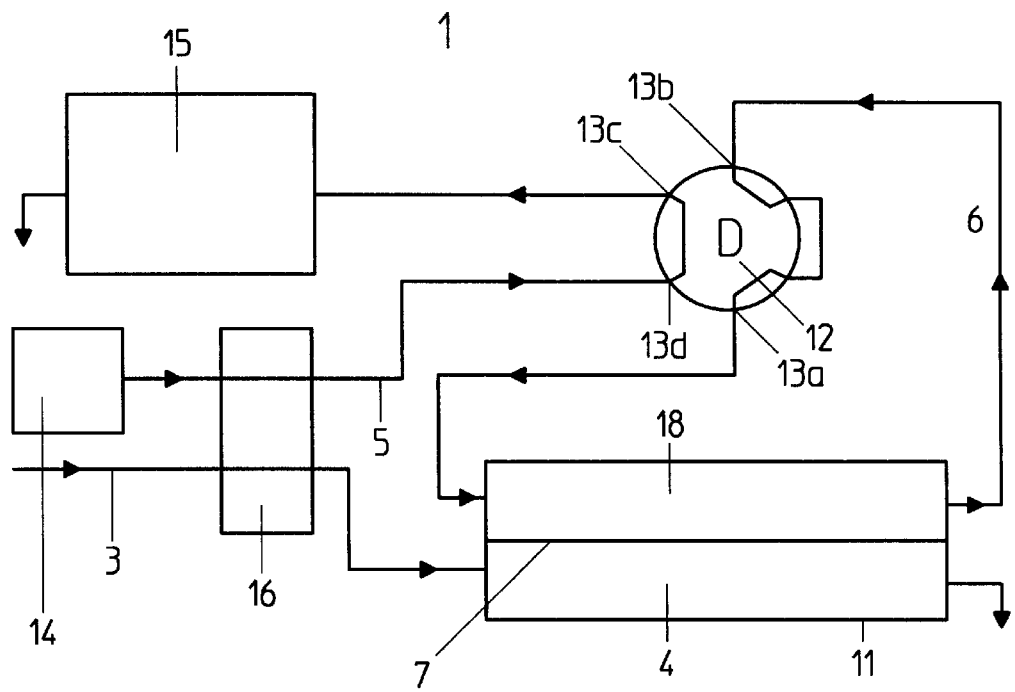

FIG. 2 shows the device according to the invention in the dialysis position D. Both openings of the acceptor chamber 18 are connected to the connections 13a, 13b of the valve 12, which for their part are connected amongst each other. The acceptor chamber 18 is, by way of this, part of an acceptor circuit 6 closed per se, the acceptor solution 5 is not renewed and is at a standstill in the acceptor circuit 6. Simultaneously, with the pump 16, the analysis solution 3 is delivered through the sample chamber 4. The solution leaving the sample chamber 4 contains a lower concentration of analytes 1 and is not longer utilised. The concentration of analytes 1 in the sample chamber 4 is 100%, even when the analytes 1 continually migrate through the membrane 7 into the acceptor chamber 18. The reduction in the concentration of analytes 1 in the sample chamber 4 is compensated by the subsequently supplied 100% analysis solution 3. As long as the concentration of the analytes 1 in the sample chamber 4 is larger than in the acceptor chamber 18, the migration of analytes from the sample chamber 4 towards the acceptor chamber 18 is larger than in the opposite direction. The concentration of the analytes 1 increases so long as the 100% analysis solution 3 is delivered through the sample chamber 4. In this manner, a concentration of the analytes 1 of approximately 100% may also be achieved in the acceptor chamber 18.

After reaching the desired analyte concentration in the acceptor circuit 6, the acceptor solution 5 is added to an analysis device 15. For this, the valve 12 is switched into an analysis position A. The analysis position A corresponds essentially to the rinsing position S shown in FIG. 1. The acceptor solution 5, containing the analytes 1, in the acceptor circuit 6 is pumped by way of the pump 16 to the analysis device 15.

Figure 3:
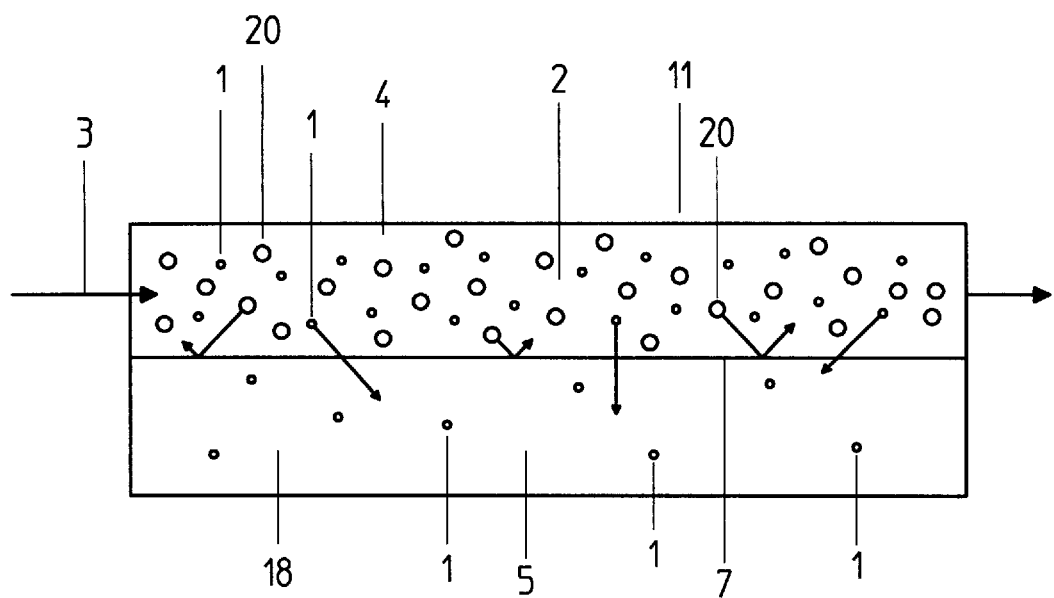

FIG. 3 shows a schematic representation of a dialysis cell 11. In the upper half of the picture there is shown a sample chamber 4 which is continually flushed with an analysis solution 3. The analysis solution 3 contains an analysis sample 2 with analytes 1 and with impurities 20. The permeable membrane 7 is chosen in a manner such that the analytes 1 may migrate into the acceptor chamber 18 containing an acceptor solution 5. The impurities 20 however are kept back by the membrane 7.

For the membrane 7, a commercially available dialysis membrane having a MWCO of 1000 is preferably employed (MWCO=Molecular Weight Cut Off), e.g. Spectraltor® CEA membrane, MWCO 1000. The dimensions of the dialysis cell 11 are e.g. 7×3 cm. The flow of the analysis solution 3 is peferably selected in a region of 0.01 to 10 milliliters per minute. In this way, it is achieved that after a dialysis time of 12 minutes, an analyte concentration of 98% to 100% is reached in the acceptor circuit 6.

The control of the pump 16 and of the valve 2 may preferably be combined with the control of a chromatograph, particularly an ion chromatograph. In this way, there results an integrated analysis unit which permits the fully automatic carrying out of a sample preparation with a directly subsequent analysis of the analysis sample.

Figure 4:
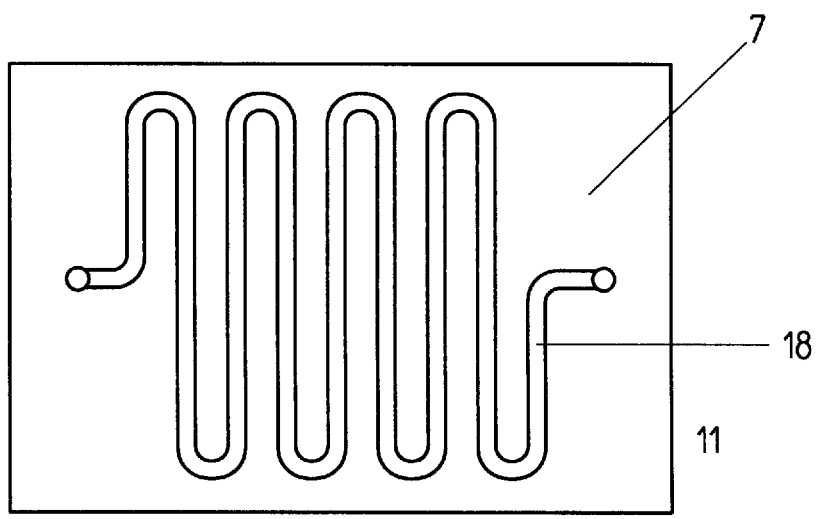

FIG. 4 shows a particularly advantageous meander-shaped arrangement of a dialysis cell 11. The acceptor chamber 18 and the sample chamber 4 (not shown in FIG. 4) are arranged meander-shaped, each on one side of the membrane 7. Similar advantageous results may also be achieved with a spiral or helical-shaped arrangement of the sample chamber and the acceptor chamber.

Figure 5A:
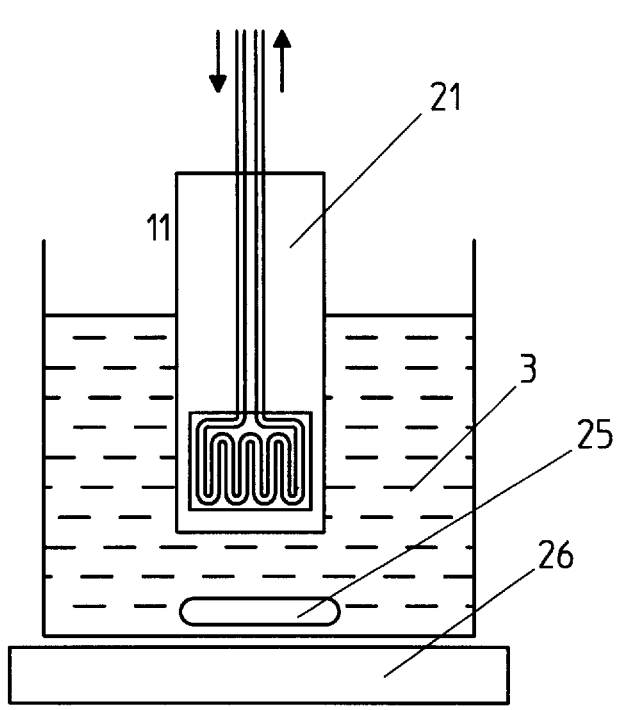
Figure 5B:
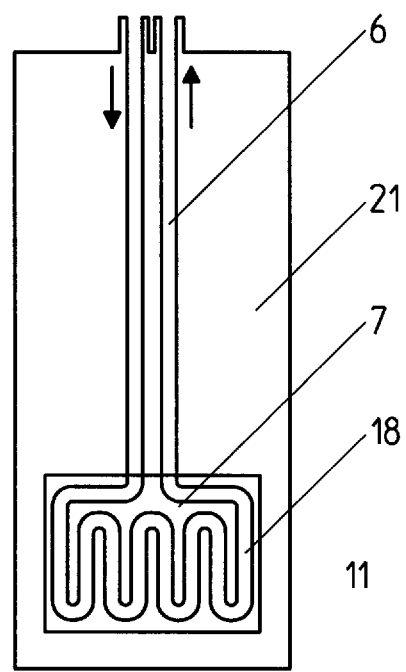

FIGS. 5a and 5b show a device according to the invention with an acceptor circuit 6 formed as a probe 21. The acceptor circuit 6 is conceived as a channel. It is delimited towards the outside by the dialysis membrane 7. The channel-shaped acceptor chamber 18 may be submersed into a receptacle having the analysis solution 3.

By way of a constant supply of fresh analysis solution 3 or by way of a continuous mixing of analysis solution 3 in a large ratio with respect to the volume of the acceptor circuit 6, the concentration of analytes in the sample chamber may be kept approximately equal to 100% during the dialysis procedure.

With the use of a stirring system 25 with a heating plate 26, one must take care that the volume of the sample solution is correctly dimensioned so that the concentration in the analysis solution reduces only negligably and a concentration of analytes in the acceptor solution of approximately 100% may be achieved. The larger the volume ratio of the analysis solution 3 compared to the acceptor solution 5 is chosen, the higher are the concentrations of analytes which may be achieved in the acceptor solution 5.

Instead of a probe with an acceptor circuit out of a channel with windings as in FIG. 5b, tubing or bag-shaped probes may be employed.

The probe may be added into a constantly moved reservoir of an analysis solution (by the supply of new analysis solution or by mixing) or be moved itself by such a reservoir. It both cases it is ensured that the one surface of the dialysis membrane is in constant contact with fresh, almost 100% analysis solution.

We claim:

1. A method for preparing samples for ion-chromatography, in a dialysis procedure, in which an analysis solution containing analytes of an analysis sample is added into a sample chamber and a determinable quantity of an acceptor solution is added into an acceptor circuit, wherein the acceptor circuit and the sample chamber are separated by a membrane permeable to the analytes and wherein the analytes diffuse from the analysis solution into the acceptor solution, said method comprising the steps of keeping the quantity of acceptor solution supplied before the beginning of dialysis procedure unchanged in the acceptor circuit during the dialysis procedure keeping the concentration of analytes in the sample chamber at least in a region neighboring the membrane substantially constant, and increasing by dialysis the concentration of analytes in the acceptor solution to a value of at least 95% of the concentration of analytes in the analysis solution.

2. A method according to claim 1, comprising a further step of analyzing the acceptor solution in a chromatograph.

3. A method according to claim 1, wherein the fresh analysis solution is continuously delivered through the sample chamber.

4. A method according to claim 3, wherein the flow of analysis solution is between 0.01 and 10 milliliters per minute, preferably 0.8 milliliters per minute.

5. A method according to claim 1, wherein a probe containing the acceptor solution and delimited by the membrane is submersed into the analysis solution.

6. A method according to claim 1, wherein the step of keeping the concentration of analytes in the sample chamber substantially constant is achieved by stirring the analysis solution in the sample chamber.

7. A method according to claim 1, wherein the step of keeping the concentration of analytes in the sample chamber substantially constant is achieved by supplying fresh analysis solution to the sample chamber.

* * * * *